United States Patent
Schacht et al.

[11] 3,968,143
[45] July 6, 1976

[54] PHENOXYPROPIONIC ACID DERIVATIVES

[75] Inventors: Erich Schacht; Günter Lauterbach; Werner Mehrhof; Herbert Nowak; Zdenek Simane, all of Darmstadt, Germany

[73] Assignee: Merck Patent Gesellschaft mit beschrankter Haftung, Darmstadt, Germany

[22] Filed: Aug. 14, 1974

[21] Appl. No.: 497,300

[30] Foreign Application Priority Data
Aug. 21, 1973 Germany............................ 2342118

[52] U.S. Cl...................... 260/473 G; 260/293.81; 260/465 F; 260/520 C; 260/544 D; 260/558 H; 260/559 D; 260/613 R; 424/267; 424/308; 424/317; 424/324
[51] Int. Cl.²......................................... C07C 69/76
[58] Field of Search........... 260/473 G, 520, 293.81

[56] References Cited
UNITED STATES PATENTS

| | | | |
|---|---|---|---|
| 3,262,850 | 7/1966 | Jones et al. | 280/473 G |
| 3,586,709 | 6/1971 | Richter et al. | 280/473 G |

OTHER PUBLICATIONS
Burger, "Medicinal Chemistry", Wiley Interscience, N.Y. (1970), pp. 71-72.

*Primary Examiner*—Paul J. Killos
*Attorney, Agent, or Firm*—Millen, Raptes & White

[57] ABSTRACT

Phenoxypropionic acid derivatives of the formula

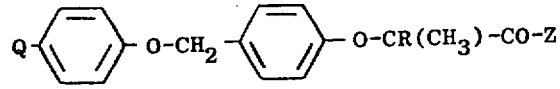

wherein Q is H or a halogen atom, R is H or $CH_3$, Z is —OH, —O-alkyl of 1–4 carbon atoms, 1-methyl-4-piperidyloxy, or —$NHCH_2CH_2OH$, and the physiologically acceptable salts thereof; possess cholesterol and triglyceride blood-level lowering activity and can be prepared, e.g., by reaction of a phenol of the formula

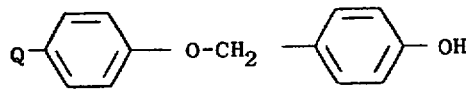

with a compound of the formula X—CR($CH_3$)—CO—Z wherein X is Cl, Br, I, or a free or esterified OH-group, and Q, R and Z have the values given above.

23 Claims, No Drawings

PHENOXYPROPIONIC ACID DERIVATIVES

BACKGROUND OF THE INVENTION

This invention relates to novel phenoxypropionic acid derivatives.

U.S. Pat. No. 3,804,839 discloses 2-p-(heterocyclic ring)- and p-(2-indanyl)-phenoxy-2-methyl-propionic acids and alkyl esters thereof having cholesterol and triglyceride blood level lowering activity. Nakamura et al., Chem. Abstracts 75, 151545 (1971), discloses corresponding compounds wherein the p-substituent on the phenyl ring is cycloalkenyl, benzothiazolyl or benzoxazolyl. Dujovne et al., Chem. Abstracts, 74, 75049, discloses corresponding compounds wherein the p-substituent is tetrahydronaphthyl (nafenopin) or chloro (clofibrate), as having cholesterol and triglyceride blood level lowering activity. The p-substituent on the phenoxy substituent of the compounds of this invention is phenoxymethyl or halophenoxymethyl.

SUMMARY OF THE INVENTION

The compounds of this invention are those of the general Formula 1

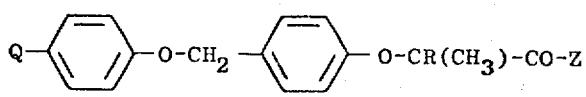

1 wherein Q is H, F, Cl, Br, or I; R is H or $CH_3$; Z is —OH, —$OR_1$, or —$NHCH_2CH_2OH$; and $R_1$ is alkyl of 1-4 carbon atoms or 1-methyl-4-piperidyl, and the physiologically acceptable salts thereof with acids and bases.

DETAILED DISCUSSION

Compounds of Formula 1 possess, with good compatibility, outstanding cholesterol blood-level-lowering and triglyceride blood-level-lowering activity, as well as enzyme-inducing effects.

The compounds of Formula 1 and their physiologically acceptable salts are useful as medicinal agents and also as intermediates for the production of other drugs.

Preferred compounds of Formula 1 are those wherein
a. Z is —OH;
b. Z is 1-methyl-4-piperidyloxy;
c. Z is methoxy or ethoxy; and
d. Q is H or Cl, especially those of (a), (b) and (c).

As will be apparent, only those compounds wherein Z is —OH can form pharmaceutically acceptable salts with bases and those wherein Z is 1-methyl-4-piperidyl can form pharmaceutically acceptable salts with acids.

In its process aspect, this invention relates to a process for the production of compounds of Formula 1 and physiologically acceptable salts thereof with acids or bases, which comprises:

a. reacting a phenol of Formula 2

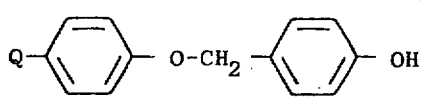

wherein Q has the values given above, with a compound of Formula 3

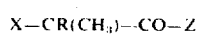  (3)

wherein X is Hal or a free or esterified OH-group, Hal being Cl, Br, or I, and R and Z have the values given above or with a haloform and acetone in the presence of a condensation agent; or b. reacting a phenol of Formula 4

  4 wherein Q has the values given above, with a compound of Formula 5

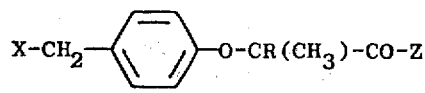  5 wherein X, R, and Z have the values given above; or c. in a compound of Formula 6

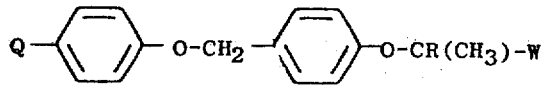

6 wherein W is a group convertible into the group —CO—Z and Q, R, and Z have the values given above, W is converted into the group —CO—Z; optionally thereafter the Z group of a thus-obtained compound of Formula 1 is converted into another Z group by treatment with a solvolyzing, thermolyzing, ester-forming, or amidating agents and/or optionally a thus-produced compound of Formula 1 wherein Z is OH is converted by treatment with a base into a physiologically acceptable metal or ammonium salt thereof or a compound of Formula 1 wherein Z is 1-methyl-4-piperidyloxy is converted with an acid into a physiologically acceptable acid addition salt thereof and/or a compound of Formula 1 is liberated from such a salt by treatment with a base or an acid, respectively.

X is preferably Cl or Br, and also especially a reactively esterified OH-group, e.g., an alkylsulfonyloxy of especially 1-6 carbon atoms (for example, methanesulfonyloxy), arylsulfonyloxy of particularly 6-10 carbon atoms (e.g., benzenesulfonyloxy, p-toluenesulfonyloxy, 1- or 2-naphthalenesulfonyloxy). X can also be 1, OH, or acyloxy, preferably of 1–7 carbon atoms (e.g., acetoxy or benzoyloxy).

The compounds of Formula 1 can be obtained particularly in accordance with methods known per se and described in the literature by reacting the phenols of Formulae 2 and 4, respectively, with compounds 3 and 5, respectively. Compounds of Formulae 3 and 4 are, for the most part, conventional and can be obtained according to known methods. The phenols 2 can be produced by reacting p-nitrobenzyl bromide with a phenol 4 to produce a p-nitrobenzyl-p'-Q-phenyl ether, reduction to the amino compound, diazotization, and hydrolysis. The compounds of Formula 5 are obtainable, for example by the reaction of p-hydroxybenzyl alcohol with a compound of Formula 3 and, if desired, subsequent conversion of the alcoholic OH-group into another X group, for example, by reaction with an inorganic acid halogenide or by acylation.

A phenol of Formula 2 or 4 can, for example, first be converted into a salt, especially a metallic salt, e.g., an alkali metal salt (Li, Na or K salt). The phenol can be reacted with a reagent forming a metallic salt, for example, an alkali metal (e.g., Na), an alkali metal hydride, or an alkali metal amide (e.g., LiH or NaH, NaNH$_2$ or KNH$_2$), a lower alkali metal alcoholate (e.g., lithium, sodium or potassium methylate, ethylate, or tert.-butylate), an organometallic compound derived from a hydrocarbon (e.g., butyllithium, phenyllithium or phenylsodium), a metal hydroxide, carbonate, or bicarbonate (e.g., of Li, Na, K or Ca). The phenolate is advantageously prepared in the presence of a solvent or solvent mixture. Suitable solvents are, for example hydrocarbons (e.g., hexane, benzene, toluene, or xylene), ethers [e.g., diethyl ether, diisopropyl ether, tetrahydrofuran (THF), dioxane, or diethylene glycol dimethyl ether], amides e.g., dimethylformamide (DMF) or hexamethylphosphoric triamide (HMPA), alcohols (e.g., methanol or ethanol), ketones (e.g., acetone or butanone).

A phenol of Formula 2 or 4 or a salt thereof is reacted with a compound of Formula 3 or 5, preferably in the presence of a diluent, for example, the solvent utilized for the production of the salt, which can, however, be replaced by or diluted by another solvent. The reaction is normally conducted at temperatures of from −20° to 150°, preferably 20° to 120°.

The metallic salt of a phenol of Formula 2 (or 4) can also be formed in situ, in which case the phenol and compound of Formula 3 and 5, respectively, are reacted with each other in the presence of a base. A particularly preferred method resides in refluxing the phenol and a compound of Formula 3 or 5 (X = Cl or Br) together with an alcoholic (e.g., ethanolic) sodium alcoholate solution for several hours.

It is also possible to react the free phenol with a hydroxy derivative of Formula 3 or 5 (X = OH), preferably in the presence of a condensation agent. Suitable condensation agents are acidic dehydration catalysts, for example, mineral acids, e.g., sulfuric acid or phosphoric acid, p-toluenesulfonyl chloride, arsenic acid, boric acid, NaHSO$_4$ or KHSO$_4$, disubstituted carbonic acid esters, e.g., diaryl carbonates (for example, diphenyl carbonate) or especially dialkyl carbonates (e.g., dimethyl or diethyl carbonate) or carbodiimides (e.g., dicyclohexylcarbodiimide). If an acid serves as the condensation agent, the reaction is advantageously effected in an excess of this acid without the addition of a further solvent, at temperatures of between 0° and 100°, preferably 50° and 60°. However, it is also possible to add diluents, e.g., benzene, toluene, or dioxane. When using a carbonate, the reaction is preferably conducted at an elevated temperature, suitably between 100° and 210°, especially between 180° and 200°, wherein a transesterification catalyst can be added, such as sodium or potassium carbonate or an alcoholate (e.g., sodium methylate).

Compounds of Formula 1 are also obtainable in accordance with methods known from the literature from compounds of Formula 6 by converting the W group thereof into the group —CO—Z, usually by solvolysis (preferably hydrolysis), or, for example, by amidation or oxidation. In particular, W is CN or CONH$_2$, but can also be one of the following (wherein R$_2$ and R$_3$ each are alkyl of 1–4 carbon atoms, preferably methyl or ethyl, and can be identical or different and, collectively, can also be tetramethylene or pentamethylene, optionally interrupted by O): CHal$_3$; COHal; COOA (wherein A is optionally substituted alkyl of up to 18 carbon atoms); C(OR$_2$)$_3$; COOAcyl (wherein Acyl is the acyl radical of a carboxylic acid of up to 18 carbon atoms); CONHR$_2$; CONR$_2$R$_3$; CONHOH; C(OH)=NOH; CONHNH$_2$; CON$_3$; C(OR$_2$)=NH; C(NH$_2$)=NNH$_2$; C(NHNH$_2$)=NH; CSOH; COSH; CSOR$_2$; CSNH$_2$; CSNHR$_2$; CSNR$_2$R$_3$; CH$_2$OH; or CHO. Compounds of Formula 6 are obtainable, for example, by the reaction of a phenol of Formula 2 with a compound of the formula X—CR(CH$_3$)—W or of a phenol of Formula 4 with a compound otherwise corresponding to Formula 5 but having a W group instead of the group —CO—Z.

Hydrolysis of compounds of Formula 6 (W=functionally modified COOH-group) can be effected in an acidic, neutral, or alkaline medium at temperatures of from −20° to 300°, preferably at the boiling point of the selected solvent. Examples of suitable acidic catalysts are hydrochloric, sulfuric, phosphoric, or hydrobromic acid; suitable basic catalysts are, e.g., sodium, potassium, or calcium hydroxide and sodium or potassium carbonate. As solvents, preferred are water; lower alcohols, e.g., methanol, ethanol; ethers, e.g., THF, dioxane; amides, e.g., DMF; nitriles, e.g., acetonitrile; sulfones, e.g., tetramethylenesulfone; or mixtures thereof, especially water-containing mixtures. However, the acid derivatives can also be saponified to carboxylic acids of Formula 1 (Z=OH), for example, in ether or benzene with the addition of a strong base, e.g., potassium carbonate, or in the absence of solvent by melting with an alkali, e.g., KOH and/or NaOH or an alkaline earth.

A preferred embodiment of the invention is the hydrolysis of amides or nitriles (6, W = CONH$_2$ or CN), which can be accomplished in an acidic medium (for example with acetic acid/HCl) or in an alkaline medium (e.g., with KOH in cyclohexanol).

It is also possible to convert acid halogenides, anhydrides and nitriles of Formula 6 (W = COHal, COOAcyl, or CN) into esters of Formula 1 (Z = OR$_1$) in accordance with methods described in the literature by reaction with an alcohol of the formula R$_1$OH, optionally in the presence of an acidic catalyst or base, e.g., NaOH, pyridine, or an alkali metal alcoholate corresponding to the alcohol employed. Preferably, an excess of the respective alcohol is used, and the reaction is carried out at temperatures of from 0° to the boiling temperature.

Esters of Formula 1 ($Z = OR_1$) can also be obtained by solvolyzing compounds of Formula 6 wherein W is a thioester, imino ether, oximino ether, hydrazone ether, thioamide, amidine, amidoxime, or amide hydrazone grouping, with a dilute aqueous base or acid, e.g., ammonia, NaOH, KOH, $Na_2CO_3$, $K_2CO_3$, HCl, $H_2SO_4$, with the addition of the respective alcohol of the formula $R_1OH$, splitting off hydrogen sulfide, ammonia, amines, hydrazine derivatives, or hydroxylamine. Most of the imino ether hydrochlorides disintegrate in an aqueous solution immediately into the esters and ammonium chlorides at room temperature. The solvolysis of some amidoximes or thioamides takes place only at temperatures of up to 100°.

It is also possible to convert compounds of Formula 6, particularly the acid halogenides (W = COHal), into the corresponding ethanolamides according to methods known per se by reaction with ethanolamine. Alcohols and aldehydes of Formula 6 (W = $CH_2OH$ and/or CHO) can be oxidized according to conventional methods, for example with $CrO_3$ or $KMnO_4$, to the carboxylic acids 1 (Z = OH).

If desired, the Z group of a thus-obtained compound of Formula 1 can be converted into another Z group by treatment with solvolyzing, thermolyzing, ester-forming or amidating agent.

A solvolysis of an ester or amide of Formula 1 (Z = $OR_1$ or $NHCH_2CH_2OH$) can be accomplished according to the above-indicated conditions, preferably by hydrolysis in an alkaline medium.

The thus-obtained esters of Formula 1 (Z = $OR_1$, especially Z = O-tert.butyl) can be converted into the corresponding acids of Formula 1 (Z = OH), by dry heating to temperatures of between 50° and 350°. The thermolysis can also be conducted in inert solvents, for example in water, DMF, dimethyl sulfoxide, cyclohexanol, ethylene glycol, or benzene, preferably with the addition of a catalytic amount of an acid, e.g., p-toluenesulfonic acid.

Esters of Formula 1 (Z = $OR_1$) can be prepared according to methods known in the literature, for example, by reacting an acid of Formula 1 (Z = OH) with the respective alcohol of the formula $R_1OH$, preferably in the presence of an inorganic or organic acid, e.g., HCl, HBr, HI, $H_2SO_4$, $H_3PO_4$, trifluoroacetic acid, benzenesulfonic acid, or p-toluenesulfonic acid, or in the presence of an acidic ion exchanger, together with or in the absence of an inert solvent, e.g., benzene, toluene, or xylene, at temperatures of from 0° to preferably the boiling temperature of the mixture. The alcohol is advantageously used in excess. The reaction can be carried out in the presence of a water-binding agent, e.g., anhydrous heavy metal salts (for example, $CuSO_4$ or $ZnCl_2$) or in the presence of a molecular sieve. It is also possible to remove the water of reaction azeotropically and, in this case, a hydrocarbon (e.g., benzene or toluene) or a chlorinated hydrocarbon (e.g., chloroform or 1,2-dichloroethane) are advantageously added. The esterification takes place under mild conditions if the water of reaction is bound chemically by adding a preferably equimolar amount of a carbodiimide (e.g., N,N'-dicyclohexylcarbodiimide), wherein inert solvents can be used, e.g., ether, dioxane, benzene or 1,2-dimethoxyethane, and a base, e.g., pyridine, can be added. The methyl ester (or ethyl ester) can also be produced by reaction of the free acid, according to processes described in the literature, with diazomethane (or diazoethane, respective) in an inert solvent, e.g., ether, benzene or methanol. Esters of Formula 1 (Z = $OR_1$) can also be prepared by chemical addition of the carboxylic acids 1 (Z = OH) to olefins (e.g., isobutylene). This chemical addition is accomplished according to methods described in this literature, preferably in the presence of a catalyst (e.g., $ZnCl_2$, $BF_3$, $H_2SO_4$, arylsulfonic acids, pyrophosphoric acid, boric acid, oxalic acid), at temperatures of from 0° to 200°, under pressures of from 1 to 300 atmospheres, and in an inert solvent, e.g., ether, THF, dioxane, benzene, toluene or xylene.

Esters of Formula 1 (Z = $OR_1$) can also be produced by the reaction of metallic salts of the acids 1 (Z = OH), preferably the alkali metal, lead, or silver salts, with alkyl halogenides corresponding to the respective alcohol, e.g., those of the formula $R_1Hal$, optionally in an inert solvent, e.g., ether, benzene or petroleum ether, or with an alkyl chlorosulfite, e.g., those of the formula $R_1OSOCl$ and thermolysis of the thus-obtained adducts.

The thus-obtained acids and esters of Formula 1 (Z = OH or $OR_1$) can be converted into the corresponding ethanolamides (Formula 1, Z = $NHCH_2CH_2OH$) by treatment with amidating agents. Most suitable as the amidating agent is ethanolamine. The amidation takes place according to conventional methods. The reaction is carried out in the presence or absence of an additional inert solvent. Suitable solvents are, for example, hydrocarbons, e.g., benzene, toluene or xylene, halogenated hydrocarbons, e.g., methylene chloride, chloroform or 1,2-dichloroethane, ethers, e.g., diethyl ether, THF or dioxane, amides, e.g., DMF, dimethylacetamide or HMPA. It is also possible to employ an excess of the ethanolamine as the solvent. The presence of a catalyst or a dehydrating agent can be advantageous. The temperatures during the amidation range suitably from about −20° to 200°. When starting with the free acids 1 (Z = OH), it is advantageous to conduct the amidation in two stages, by first converting the free acid into an acid halogenide, for example, into the chloride with thionyl chloride, and then reacting the product with ethanolamine.

The compounds of Formula 1 can be present in an optionally inactive form or, when they contain a center of asymmetry, also in an optically active form. Racemates of Formula 1 can be separated into the optical antipodes thereof by means of methods disclosed in the literature. Carboxylic acids of Formula 1 (Z = OH) can be converted, for example, with optically active amines, e.g., quinine, brucine, or strychnine, into diastereomeric salts which can be separated by crystallization and split up by hydrolysis.

A basic compound of Formula 1 (R = 1-methyl-4-piperidyl) can be converted into an acid addition salt thereof with an acid. Suitable for this reaction are acids yielding physiologically acceptable salts, including both organic and inorganic acids, e.g., aliphatic, alicyclic, araliphatic, aromatic and heterocyclic, mono- or polybasic carboxylic and sulfonic acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, aminocarboxylic acids, sulfamic acid, benzoic acid, salicyclic acid, 2-phenylpropionic acid, citric acid, gluconic acid, ascorbic acid, nicotinic acid, isonicotinic acid, methanesulfonic acid, ethanedisulfonic acid, 2-hydroxyethanesulfonic acid, p-toluenesulfonic acid, naphthalene-mono- and -disulfonic acids, sulfuric acid, nitric acid, hydrohalic acids, e.g., hydrochloric acid and hydrobromic acid, and phosphoric acids, e.g., orthophosphoric acid.

The acidic compounds of Formula 1 (Z = OH) can be converted, by reaction with a base, into a physiologically acceptable metal or ammonium salt. Especially suitable salts are the sodium, potassium, magnesium, calcium, and ammonium and substituted ammonium salts.

Conversely, compounds of Formula 1 can be liberated from the acid addition salts thereof by treatment with strong bases and/or from the metal and ammonium salts thereof by treatment with acids.

The compounds of Formula 1 and/or the physiologically acceptable salts thereof can be employed as medicinal agents in human or veterinary medicine, in admixture with solid, liquid and/or semiliquid excipients. Suitable vehicles are those organic or inorganic substances suitable for parenteral, enteral, or topical application and which do not react with the novel compounds, such as, for example, water, vegetable oils, benzyl alcohols, polyethylene glycols, gelatin, lactose, amylose, magnesium stearate, talc, vaseline, cholesterol. Suitable for parenteral application are, furthermore, solutions, preferably oily or aqueous solutions, as well as suspensions, emulsions, or implants. For enteral administration, suitable are tablets, dragees, capsules, syrups, elixirs, or suppositories, and for topical administration, ointments, creams, or powders. The above-indicated preparations can optionally be sterilized or contain auxliary substances, such as lubricants, preservatives, stabilizers, or wetting agents, emulsifiers, salts for influencing the osmotic pressure, buffers, coloring, flavoring and/or aromatic substances.

The substances are preferably administered in doses of between 10 and 1000 mg. per dosage unit.

In particular, the substances are preferably administered in doses of between 30 and 300 mg. per dosage unit. The daily dose is preferably between about 0.2 and 20 mg. per kg. body weight. Oral application is preferred.

The cholesterol and the triglyceride blood-level-lowering activities can be demonstrated in the serum of rats according to the methods of Levine et al. (Automation in Analytical Chemistry, Technicon Symposium, 1967, Mediad, N.Y., pp. 25 – 28) and Noble and Campbell (Clin. Chem., vol 16, pp. 166 – 170, 1970), respectively.

The temperatures herein are indicated in degrees Celsius. "Working up as usual" means the following: If necessary, water is added; the mixture is extracted with ethyl acetate, ether, or chloroform; the product is separated; the organic extract is washed with water, dried over sodium sulfate, filtered, and evaporated; and the thus-obtained product is purified by distillation or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 2.3 g. of sodium is dissolved in 100 ml. of absolute ethanol; 20 g. of 4-phenoxymethylphenol and 18.1 g. of the ethyl ester of 2-bromopropionic acid are added thereto, and the mixture is refluxed for 3 hours and evaporated. After working up the mixture as usual, the ethyl ester of 2-(4-phenoxymethylphenoxy)-propionic acid is obtained.

Analogously, with the use of the following starting compounds:
    4-p-fluorophenoxymethylphenol
    4-p-chlorophenoxymethylphenol
    4-p-bromophenoxymethylphenol
    4-p-iodophenoxymethylphenol
the following final products are obtained with the ethyl ester of 2-chloro-, 2-bromo-, or 2-iodopropionic acid:
    ethyl ester of 2-(4-p-fluorophenoxymethylphenoxy)-propionic acid
    ethyl ester of 2-(4-p-chlorophenoxymethylphenoxy)-propionic acid
    ethyl ester of 2-(4-p-bromophenoxymethylphenoxy)-propionic acid
    ethyl ester of 2-(4-p-iodophenoxymethylphenoxy)-propionic acid.

Analogously, the products set forth below are produced with the ethyl ester of 2-chloro-, 2-bromo-, or 2-iodoisobutyric acid:
    ethyl ester of 2-(4-phenoxymethylphenoxy)-2-methylpropionic acid
    ethyl ester of 2-(4-p-fluorophenoxymethylphenoxy)-2-methylpropionic acid, m.p. 54°–55°
    ethyl ester of 2-(4-p-chlorophenoxymethylphenoxy)-2-methylpropionic acid
    ethyl ester of 2-(4-p-bromophenoxymethylphenoxy)-2-methylpropionic acid
    ethyl ester of 2-(4-p-iodophenoxymethylphenoxy)-2-methylpropionic acid.

b. 7 g. of the ethyl ester of 2-(4-phenoxymethylphenoxy)-propionic acid is refluxed with 7 g. of KOH in 70 ml. of ethanol for 2 hours. The mixture is then evaporated, dissolved in water, washed with ether, acidified, and worked up as usual, thus obtaining 2-(4-phenoxymethylphenoxy)-propionic acid.

Analogously, the following products are obtained by the saponification of the corresponding esters:
    2-(4-p-fluorophenoxymethylphenoxy)-propionic acid
    2-(4-p-chlorophenoxymethylphenoxy)-propionic acid
    2-(4-p-bromophenoxymethylphenoxy)-propionic acid
    2-(4-p-iodophenoxymethylphenoxy)-propionic acid
    2-(4-phenoxymethylphenoxy)-2-methylpropionic acid, m.p. 122°–124°
    2-(4-p-fluorophenoxymethylphenoxy)-2-methylpropionic acid, m.p. 123°–125°
    2-(4-p-chlorophenoxymethylphenoxy)-2-methylpropionic acid, m.p. 151°–153°
    2-(4-p-bromophenoxymethylphenoxy)-2-methylpropionic acid, m.p. 170°–172°
    2-(4-p-iodophenoxymethylphenoxy)-2-methylpropionic acid.

c. 5 g. of 2-(4-phenoxymethylphenoxy)-propionic acid is dissolved in 200 ml. of saturated methanolic hydrochloric acid; the mixture is allowed to stand for 12 hours at room temperature, refluxed for 2 hours, and evaporated. The usual working up operation yields the methyl ester of 2-(4-phenoxymethylphenoxy)-propionic acid.

Analogously, the corresponding methyl, ethyl, n-propyl, isopropyl, n-butyl, isobutyl, and/or sec.-butyl esters, for example the ethyl ester, n-propyl ester, isopropyl ester, n-butyl ester, isobutyl ester and/or sec.-butyl ester of 2-(4-phenoxymethylphenoxy)-propionic acid are obtained from the acids set forth under (b) by reaction with HCl in methanol, ethanol, n-propanol, isopropanol, n-butanol, isobutanol, and sec.-butanol, respectively.

d. One gram of 2-(4-phenoxymethylphenoxy)-propionic acid is dissolved in 20 ml. of ether and combined dropwise with etherdiazomethane solution until the yellow coloring is permanent. After evaporation, the methyl ester of 2-(4-phenoxymethylphenoxy)-propionic acid is obtained.

Analogously, the following compounds are produced from the corresponding acids with diazomethane:

the methyl ester of each of the following acids:
2-(4-p-fluorophenoxymethylphenoxy)-propionic acid
2-(4-chlorophenoxymethylphenoxy)-propionic acid
2-(4-p-bromophenoxymethylphenoxy)-propionic acid
2-(4-p-iodophenoxymethylphenoxy)-propionic acid
2-(4-phenoxymethylphenoxy)-2-methylpropionic acid
2-(4-p-fluorophenoxymethylphenoxy)-2-methylpropionic acid
2-(4-p-chlorophenoxymethylphenoxy)-2-methylpropionic acid
2-(4-p-bromophenoxymethylphenoxy)-2-methylpropionic acid
2-(4-p-iodophenoxymethylphenoxy)-2-methylpropionic acid.

e. 2.72 g. of 2-(4-phenoxymethylphenoxy)-propionic acid is dissolved in 12 ml. of HMPA and mixed, at 10°, with 0.72 ml. of thionyl chloride. After two hours of agitation at −5°, 1.23 g. of 1-methyl-4-hydroxypiperidine is added. The mixture is agitated overnight at 20°, poured on water, and worked up as usual, thus obtaining the (1-methyl-4-piperidyl) ester of 2-(4-phenoxymethylphenoxy)-propionic acid.

Analogously, the (1-methyl-4-piperidyl) esters of each of the following acids are correspondingly obtained:
2-(4-p-fluorophenoxymethylphenoxy)-propionic acid
2-(4-p-chlorophenoxymethylphenoxy)-propionic acid
2-(4-p-bromophenoxymethylphenoxy)-propionic acid
2-(4-p-iodophenoxymethylphenoxy)-propionic acid
2-(4-phenoxymethylphenoxy)-2-methylpropionic acid
2-(4-p-fluorophenoxymethylphenoxy)-2-methylpropionic acid
2-(4-p-chlorophenoxymethylphenoxy)-2-methylpropionic acid, fumarate, m.p. 134°–135°
2-(4-p-bromophenoxymethylphenoxy)-2-methylpropionic acid
2-(4-p-iodophenoxymethylphenoxy)-2-methylpropionic acid.

f. 2.72 g. of 2-(4-phenoxymethylphenoxy)-propionic acid is dissolved in 12 ml. of HMPA. At −10°, 0.77 ml. of thionyl chloride is added thereto, and the mixture is agitated for 2 hours at −5°. Thereafter, 2.5 ml. of ethanolamine is added and the reaction mixture is stirred overnight at 20°. The mixture is then poured on ice and worked up as usual, yielding the 2-hydroxyethylamide of 2-(4-phenoxymethylphenoxy)-propionic acid.

Analogously, the 2-hydroxyethyl amides of each of the following acids are correspondingly obtained:
2-(4-p-fluorophenoxymethylphenoxy)-propionic acid
2-(4-p-chlorophenoxymethylphenoxy)-propionic acid
2-(4p-bromophenoxymethylphenoxy)-propionic acid
2-(4-p-iodophenoxymethylphenoxy)-propionic acid
2-(4-phenoxymethylphenoxy)-2-methyl-propionic acid
2-(4-p-flurophenoxymethylphenoxy)-2methylpropionic acid
2-(4-p-chlorophenoxymethylphenoxy)-2-methylpropionic acid, m.p. of the 2-hydroxyethylamide: 110°–112°
2-(4-p-bromophenoxymethylphenoxy)-2-methylpropionic acid
2-(4-p-iodophenoxymethylphenoxy)-2-methylpropionic acid.

EXAMPLE 2

A mixture of 20 g. of 4-phenoxymethylphenol and 13.2 g. of the ethyl ester of 2-hydroxyisobutyric acid is combined with 15 g. of sulfuric acid, and the reaction mixture is agitated for 2 hours at 50°–60°. After cooling, the mixture is combined with water and worked up as usual, obtaining the ethyl ester of 2-(4-phenoxymethylphenoxy)-2methyl-propionic acid.

EXAMPLE 3

20 g. of 4-phenoxymethylphenol is dissolved in 200 ml. of acetone. Under agitation, 4 g. of NaOH is added dropwise to the reaction mixture, and then, under stirring and boiling, 16.7 g. of 2-bromoisobutyric acid is added dropwise thereto (or 12.25 g. of 2-chloroisobutyric acid is used instead) in 60 ml. of acetone. The mixture is agitated for 1 hour at 56° and allowed to stand for 24 hours. The acetone is distilled off, and the residue is worked up as usual, thus producing 2-(4-phenoxymethylphenoxy)-2-methylpropionic acid.

EXAMPLE 4

At 40°–50°, 30 g. of chloroform is added dropwise to a mixture of 20 g. of 2-phenoxymethylphenol, 100 ml. of acetone, and 21 g. of pulverized potassium hydroxide. The mixture is refluxed for 12 hours, evaporated, mixed with water, and worked up as usual, thus obtaining 2-(4-phenoxymethylphenoxy)-2-methylpropionic acid.

EXAMPLE 5

2.3 g. of sodium is dissolved in 250 ml. of absolute ethanol; 9.4 g. of phenol and 28.6 g. of the ethyl ester of 2-(p-bromomethylphenoxy)-propionic acid [obtainable by reacting p-hydroxybenzyl alcohol with ethyl 2-bromopropionate to the ethyl ester of 2-(p-hydroxymethylphenoxy)-propionic acid and subsequent reaction with $SOBr_2$] are added thereto, and the mixture is refluxed for 3 hours and evaporated. The usual working-up procedure yields the ethyl ester of 2-(4-phenoxymethylphenoxy)-propionic acid.

Analogously, the ethyl ester of 2-(4-phenoxymethylphenoxy)-2-methylpropionic acid is obtained from the ethyl ester of 2-p-bromomethylphenoxyisobutyric acid (obtainable by bromination of the ethyl ester of 2-p-methylphenoxyisobutyric acid with N-bromosuccinimide);

and the remaining esters set forth in Example 1(a) are produced with p-fluorophenol, p-chlorophenol, p-bromophenol, and p-iodophenol, respectively.

EXAMPLE 6

One gram of 2-(4-phenoxymethylphenoxy)-propionitrile (obtainable from 4-phenoxymethylphenol and 2-bromopropionitrile) is refluxed in 15 ml. of ethanol and 2 ml. of water with 2 g. of KOH for 40 hours. The mixture is then evaporated and worked up as usual, yielding 2-(4-phenoxymethylphenoxy)-propionic acid.

EXAMPLE 7

One gram of 2-(4-phenoxymethylphenoxy)-propionitrile is refluxed for 2 hours with 6 ml. of acetic acid and 6 ml. of concentrated hydrochloric acid. The mixture is evaporated, the residue dissolved in dilute sodium hydroxide solution, washed with ether, and worked up as usual, thus obtaining 2-(4-phenoxymethylphenoxy)-propionic acid.

EXAMPLE 8

The iminoethyl ether hydrochloride of 2-(4-phenoxymethylphenoxy)-propionic acid [obtainable from 2-(4-phenoxymethylphenoxy)-propionitrile and ethanol/HCl in ether at 0°] is refluxed for one hour with 25 ml. of water. After the mixture has been worked up as usual, the ethyl ester of 2-(4-phenoxymethylphenoxy)-propionic acid is produced.

EXAMPLE 9

One gram of 2-(4-phenoxymethylphenoxy)-propionamide (obtainable from the nitrile with sulfuric acid at 25°) and 2 g. of KOH are refluxed in 40 ml. of ethanol for 3 hours; after evaporation, the mixture is worked up as usual, yielding 2-(4-phenoxymethylphenoxy)-propionic acid.

EXAMPLE 10

A mixture of 1 g. of 2-(4-phenoxymethylphenoxy)-propionamide, 2 ml. of concentrated hydrochlorid acid, and 2 ml. of acetic acid is refluxed for 48 hours and, after adding water, worked up as usual, yielding 2-(4-phenoxymethylphenoxy)-propionic acid.

The following examples relate to pharmaceutical preparations containing phenoxypropionic acid derivatives of general Formula 1:

EXAMPLE A: Tablets

A mixture consisting of
- 300 kg. of 2-(4-p-fluorophenoxymethylphenoxy)-2-methylpropionic acid,
- 500 kg. of lactose,
- 160 kg. of corn starch,
- 20 kg. of cellulose powder, and
- 20 kg. of magnesium stearate is compressed to tablets in the usual manner so that each tablet contains 300 mg. of the active agent.

EXAMPLE B: Dragees

Tablets are compressed in accordance with Example A and then coated in the usual manner with a layer of sugar, corn starch, talc, and tragacanth.

Analogously, tablets and dragees are obtainable which contain one or more of the remaining effective agents of Formula 1 and/or the physiologically acceptable salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A phenoxypropionic acid derivative of the formula

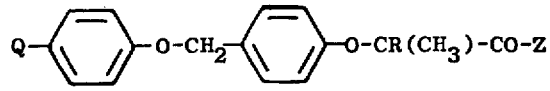

wherein Q is H or halogen, R is H or $CH_3$, Z is —OH or —$OR_1$, and $R_1$ is alkyl of 1–4 carbon atoms or 1-methyl-4-piperidyl, and the physiologically acceptable salts thereof.

2. A compound of claim 1 wherein Z is —OH, methoxy, ethoxy or 1-methyl-4-piperidyloxy.
3. A compound of claim 1 wherein Q is H or Cl.
4. A compound of claim 1, 2-(4-phenoxymethylphenoxy)-propionic acid.
5. A compound of claim 1, ethyl ester of 2-(4-phenoxymethylphenoxy)-propionic acid.
6. A compound of claim 1, 2-(4-p-fluorophenoxymethylphenoxy)-propionic acid.
7. A compound of claim 1, ethyl ester of 2-(4-p-fluorophenoxymethylphenoxy)-propionic acid.
8. A compound of claim 1, 2-(4-p-chlorophenoxymethylphenoxy)-propionic acid.
9. A compound of claim 1, ethyl ester of 2-(4-p-chlorophenoxymethylphenoxy)-propionic acid.
10. A compound of claim 1, 2-(4-phenoxymethylphenoxy)-2-methylpropionic acid.
11. A compound of claim 1, ethyl ester of 2-(4-phenoxymethylphenoxy)-2-methylpropionic acid.
12. A compound of claim 1, 2-(4-p-fluorophenoxymethylphenoxy)-2-methylpropionic acid.
13. A compound of claim 1, ethyl ester of 2-(4-p-fluorophenoxymethylphenoxy)-2-methylpropionic acid.
14. A compound of claim 1, (1-methyl-4-piperidyl) ester of 2-(4-p-fluorophenoxymethylphenoxy)-2-methylpropionic acid.
15. A compound of claim 1, 2-(4-p-chlorophenoxymethylphenoxy)-2-methylpropionic acid.
16. A compound of claim 1, ethyl ester of 2-(4-p-chlorophenoxymethylphenoxy)-2-methylpropionic acid.
17. A compound of claim 1, (1-methyl-4-piperidyl) ester of 2-(4-p-chlorophenoxymethylphenoxy)-2-methylpropionic acid.
18. A compound of claim 1, 2-(4-p-bromophenoxymethylphenoxy)-2-methylpropionic acid.
19. A compound of claim 1, ethyl ester of 2-(4-p-bromophenoxymethylphenoxy)-2-methylpropionic acid.
20. A compound of claim 1, 2-(4-p-iodophenoxymethylphenoxy)-2-methylpropionic acid.
21. A compound of claim 1, ethyl ester of 2-(4-p-iodophenoxymethylphenoxy)-2-methylpropionic acid.
22. A compound of claim 1 wherein Z is OH.
23. A compound of claim 1 wherein Z is methoxy or ethoxy.

* * * * *